(12) United States Patent
Haslett et al.

(10) Patent No.: US 7,625,117 B2
(45) Date of Patent: Dec. 1, 2009

(54) BANDAGE WITH SENSORS

(76) Inventors: James W. Haslett, 17 Cullen Creek Estates, Calgary, AB (CA) T3Z 3K8; Ivars Finvers, 171 Scanlon Green NW, Calgary, AB (CA) T3L 1M3; Graham A Jullien, 4030 Garrison Blvd SW, Calgary, AB (CA) T2T 6J6

( * ) Notice: Subject to any disclaimer, the term of this patent is extended or adjusted under 35 U.S.C. 154(b) by 139 days.

(21) Appl. No.: 11/681,628

(22) Filed: Mar. 2, 2007

(65) Prior Publication Data

US 2007/0206655 A1    Sep. 6, 2007

(30) Foreign Application Priority Data

Mar. 3, 2006   (CA)   ................................. 2538940

(51) Int. Cl.
*G01K 3/00* (2006.01)
*G01K 7/00* (2006.01)

(52) U.S. Cl. .............. 374/111; 374/133; 374/166; 600/474

(58) Field of Classification Search ............... 374/109, 374/111, 115, 133, 163, 166–167, 170, 181; 600/549

See application file for complete search history.

(56) References Cited

U.S. PATENT DOCUMENTS

| | | | | |
|---|---|---|---|---|
| 3,597,976 A * | 8/1971 | Fryar | ........................... | 374/106 |
| 6,086,247 A * | 7/2000 | von Hollen | .................. | 374/137 |
| 6,090,050 A * | 7/2000 | Constantinides | ............ | 600/549 |
| 6,292,685 B1 | 9/2001 | Pompei | | |
| 6,315,719 B1 * | 11/2001 | Rode et al. | ................... | 600/300 |
| 6,416,471 B1 | 7/2002 | Kumar et al. | | |
| 6,447,460 B1 * | 9/2002 | Zheng et al. | ................. | 600/549 |
| 6,499,877 B2 | 12/2002 | Pompei | | |
| 6,547,745 B1 * | 4/2003 | Rubinstein | ................... | 600/549 |
| 6,646,567 B1 | 11/2003 | Olivas | | |
| 6,709,154 B1 * | 3/2004 | Janotte | ........................ | 374/121 |
| 6,847,913 B2 * | 1/2005 | Wigley et al. | ................ | 702/131 |
| 6,890,096 B2 | 5/2005 | Tokita et al. | | |
| 6,898,457 B1 * | 5/2005 | Kraus et al. | ................... | 600/474 |
| 6,929,611 B2 | 8/2005 | Koch | | |
| 6,932,775 B2 | 8/2005 | Pompei et al. | | |
| 6,963,772 B2 * | 11/2005 | Bloom et al. | ................ | 600/547 |
| 7,213,969 B2 * | 5/2007 | Russak et al. | ................ | 374/208 |
| 7,340,293 B2 * | 3/2008 | McQuilkin | ................... | 600/474 |
| 2001/0044588 A1 * | 11/2001 | Mault | ........................... | 600/549 |
| 2001/0047127 A1 * | 11/2001 | New et al. | .................... | 600/300 |

(Continued)

OTHER PUBLICATIONS

F. Pompei and M. Pompei, "Non-invasive temporal artery thermometry: Physics, physiology, and clinical accuracy," in Proceedings of SPIE, M. R. Dury, E. T. Theocharous, N. J. Harrison, M. Hilton, and N. Fox, Eds., vol. 5405, Apr. 2004, pp. 61-67.

(Continued)

*Primary Examiner*—Patrick J Assouad
*Assistant Examiner*—Bret Adams
(74) *Attorney, Agent, or Firm*—Stephen M. Nipper; Dykas, Shaver & Nipper, LLP

(57) ABSTRACT

A bandage incorporates sensor arrays. The sensor arrays may measure temperature and are fixed to a person's temple in use, or other suitable body part. An estimate of core body temperature may be made using the arrays. The bandage may carry processing electronics and a transmitter. Processing may be done on the bandage or remotely from the bandage. Other physiological parameters may be measured depending on the type of sensor used.

8 Claims, 5 Drawing Sheets

U.S. PATENT DOCUMENTS

| | | | | |
|---|---|---|---|---|
| 2002/0143257 | A1* | 10/2002 | Newman et al. | 600/474 |
| 2003/0149349 | A1* | 8/2003 | Jensen | 600/372 |
| 2004/0170216 | A1* | 9/2004 | Russak et al. | 374/208 |
| 2005/0245839 | A1* | 11/2005 | Stivoric et al. | 600/549 |
| 2006/0047218 | A1* | 3/2006 | Bloom et al. | 600/547 |
| 2006/0161074 | A1* | 7/2006 | Liao | 600/549 |
| 2006/0173375 | A1* | 8/2006 | Koch | 600/549 |
| 2006/0264730 | A1* | 11/2006 | Stivoric et al. | 600/390 |
| 2007/0100666 | A1* | 5/2007 | Stivoric et al. | 705/3 |
| 2008/0008225 | A1* | 1/2008 | Ahmad et al. | 374/109 |

OTHER PUBLICATIONS

D. Fiala, K. J. Lomas, and M. Stohrer, "A computer model of human thermoregulation for a wide range of environmental conditions: the passive system." J Appl Physiol, vol. 87, No. 8750-7587, pp. 1957-1972, 1999.

Y. H. Chiok, E. Y.-K. Ng, and V. V. Kulish, "Global bioheat model for quick evaluation of the human physiological thermal profiles under differing conditions." J Med Eng Technol, vol. 26, No. 0309-1902, pp. 231-238, 2002.

Z.-S. Deng and J. Liu, "Mathematical modeling of temperature mapping over skin surface and its implementation in thermal disease diagnostics." Comput Biol Med, vol. 34, No. 0010-4825, pp. 495-521, 2004.

S. B. Wilson and V. A. Spence, "A tissue heat transfer model for relating dynamic skin temperature changes to physiological parameters." Phys Med Biol, vol. 33, No. 0031-9155, pp. 895-912, 1988.

* cited by examiner

BANDAGE WITH SENSORS

BACKGROUND

Core body temperature is an important indicator of a person's health. Traditionally non-invasive measurement of body temperature is based on oral, rectal, tympanic (ear), or axial (armpit) thermometers. Typically these provide a single temperature measurement per use and are not used to provide long-term monitoring of a patient's temperature. More recently, clinical thermometers based on the measurement of skin temperature over the superficial temporal artery of the forehead have appeared. The current implementations of these thermometers are as hand-held wands that are manually scanned across the forehead region. For long term monitoring of body temperature a thermometer that is unobtrusive and can be left affixed to a patient is needed.

SUMMARY

In one embodiment, a device is provided to estimate the core body temperature based on multiple temperature measurements made on a body surface for example in the temple region of the forehead. The core temperature may be estimated using temperatures measured locally to the bandage. The temperature sensing device may be affixed to the forehead region as a small flexible bandage. Raw sensor data may be transmitted to a remote receiver.

According to other embodiments, the device can be used for other measurements, and therefore there is also provided a measuring device, comprising: a bandage; an array of sensors attached to the bandage, the sensors of the array of sensors having sensing surfaces; and the sensors of the array of sensors having an output.

According to another embodiment, there is provided a non-invasive means of estimating core body temperature using a multi-sensor thermometer that is constructed in a flexible bandage like form and affixed to the temple region of a patient's forehead.

In a further embodiment, there is provided a system for measurement of core body temperature which includes a device that is affixed to the forehead in the region of the temple, and a device to receive and process the sensor data transmitted wirelessly by the device affixed to the forehead.

According to a further embodiment, a device affixed to the temple region of the forehead is provided as a flexible bandage. The bandage includes two arrays of temperature sensors. The first array of temperature sensors is positioned on the bottom surface of the bandage and provides a set of measurements of temperature of the skin that is underneath each sensor. The second temperature sensor array is positioned towards the outer surface (away from the skin) of the bandage and is separated from the first temperature array by a layer of thermally insulating material. An electronic circuit is used to measure the output of each temperature sensor in each array. A processor converts the sensor readings into an equivalent temperature reading. Conversion of temperature sensor array measurements to an estimated core body temperature reading may be performed partially or entirely locally to a bandage or remotely, for example after wireless transmission to a receiver. The receiver may display the body temperature directly, and may send the information to other systems used to monitor and record patient medical information. Methods of measuring the temperature of a body are also provided.

BRIEF DESCRIPTION OF THE DRAWINGS

There will now be described embodiments of a bandage with sensors, by reference to the figures by way of example, in which like numerals denote like elements, and in which.

DETAILED DESCRIPTION

In the claims, the word "comprising" is used in its inclusive sense and does not exclude other elements being present. The indefinite article "a" before a claim feature does not exclude more than one of the feature being present. Each one of the individual features described here may be used in one or more embodiments and is not, by virtue only of being described here, to be construed as essential to all embodiments as defined by the claims.

Figure 1:
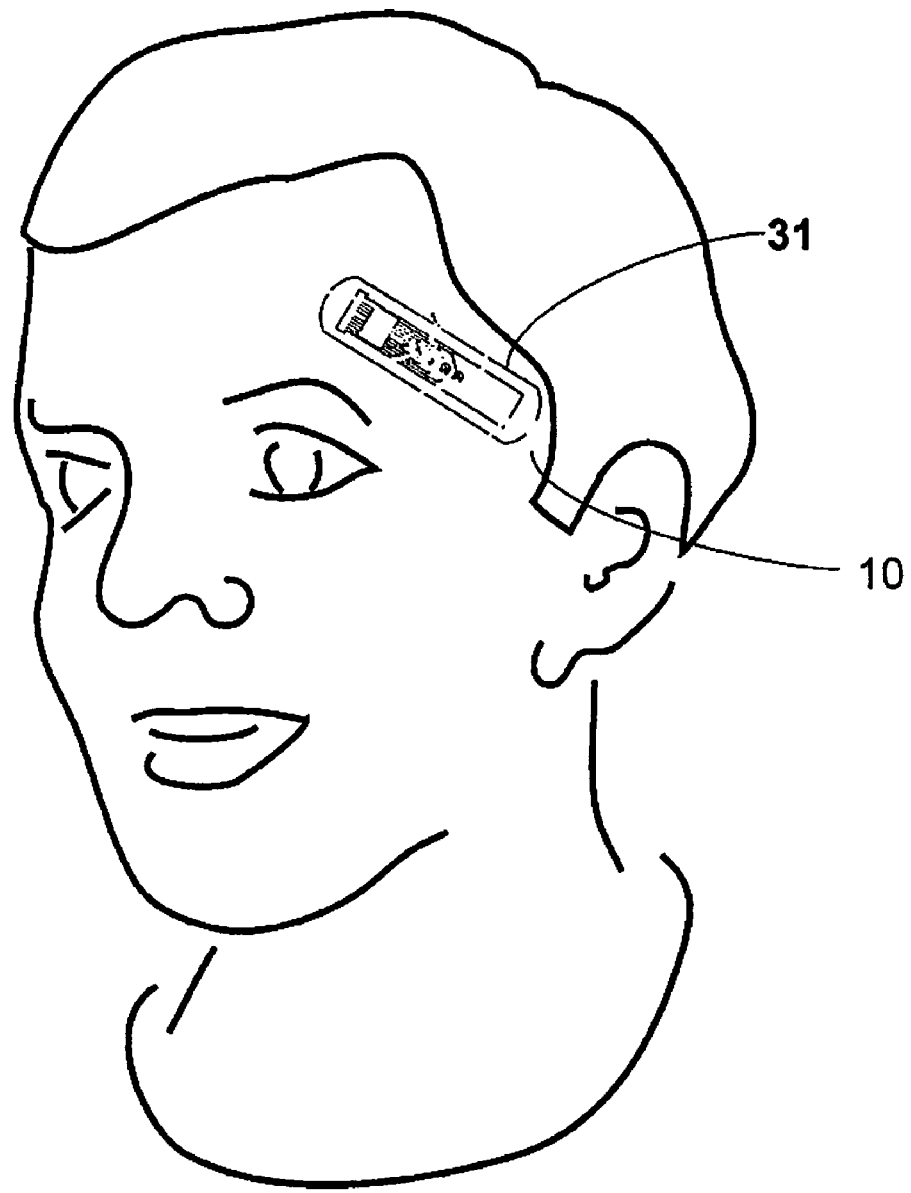
FIG. 1 shows a bandage thermometer positioned on the forehead in the temple region.
Figure 2:
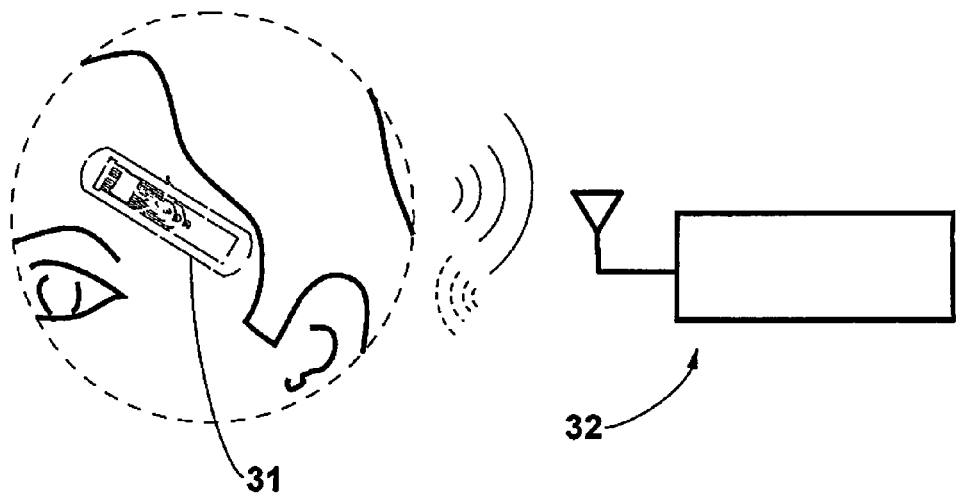
FIG. 2 shows a bandage thermometer positioned on the forehead in the temple region along with the remote receiver.
Figure 3:
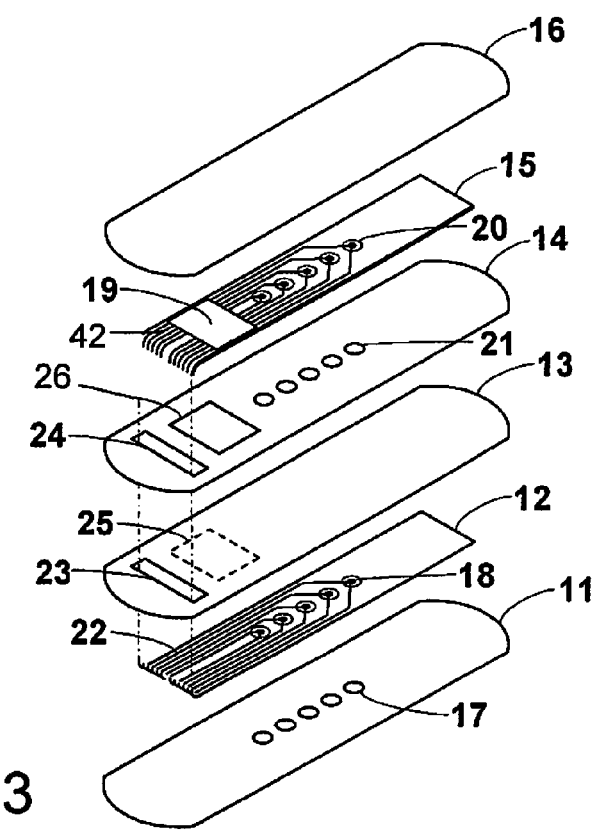
FIG. 3 shows an exploded view of one embodiment of the bandage thermometer.
Figure 4:
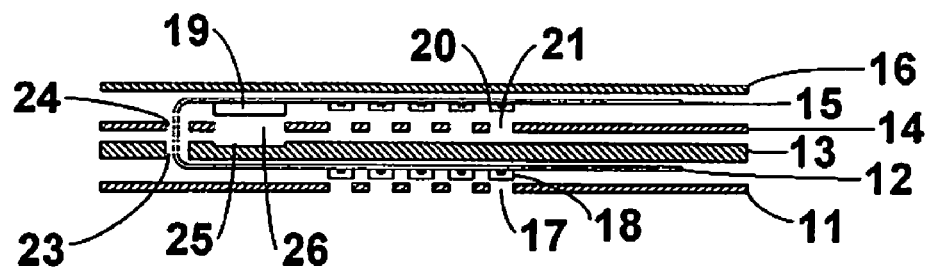
FIG. 4 shows an exploded view of the cross-sectional view of one embodiment of the bandage thermometer.
Figure 5:
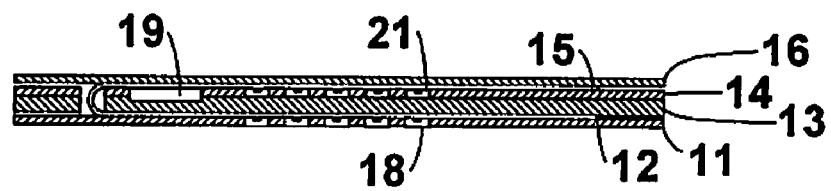
FIG. 5 shows a cross-sectional view of one embodiment of the bandage thermometer.

As shown in FIG. 1, for example, an embodiment of a bandage thermometer 31 is affixed to the forehead in the temple region. In this position, the bandage may overlay a portion of the superficial temporal artery 30 that lies just beneath the skin surface in this region. The bandage can be equally affixed to either the left or right temple region of a patient's forehead, or any other position in which a parameter is to be sensed.

In one embodiment, in order to estimate core body temperature of a person, the temperature of the skin ($T_{skin}$), which in one embodiment is skin overlying a portion of the superficial temporal artery, is measured along with a second temperature ($T_{outer}$) that is used to subsequently estimate the heat flowing out of the skin in this region. By combining the two temperatures, the core body temperature $T_{core}$ can be estimated using:

$$T_{core} = T_{skin} + \alpha(T_{skin} - T_{outer}) \tag{1}$$

where $T_{skin}$ may represent the temperature of the skin in a region in close proximity to the superficial temporal artery, and $T_{outer}$ may represent the temperature of an outer temperature sensor which is in close, or in closest, proximity to the skin temperature sensor which provided the $T_{skin}$ measurement.

The parameter $\alpha$ is an empirically determined coefficient which depends upon the physical construction and thermal characteristics of the bandage, and the physical location of the temporal artery relative to the bandage and the thermal characteristic of the tissue separating the artery from the temperature sensor. The physical and thermal characteristics of the bandage can be well controlled by its construction. The location of the artery and thermal characteristics of the overlying tissue will vary with each individual and with each particular placement of the bandage. Therefore α is best determined through the use of clinical trials using a specific implementation of the bandage.

Figure 7:
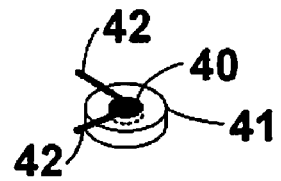
FIG. 7 shows one of the temperature sensor elements.
Figure 6:
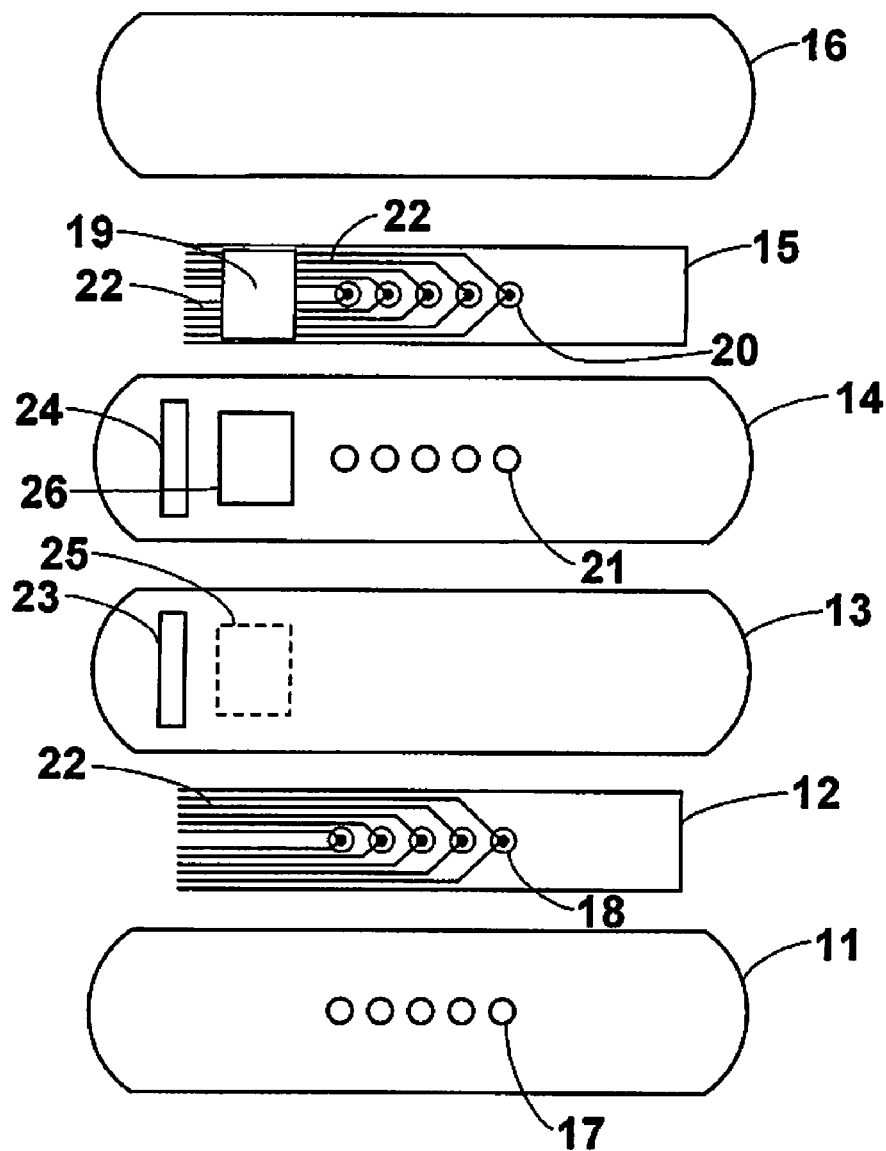
FIG. 6 shows a bottom view of one embodiment of the bandage thermometer.

In an embodiment of a bandage with sensors shown in FIGS. 3-6, multiple temperature sensors 18 may be arrayed longitudinally along the bottom surface (the surface facing towards the skin) of a bandage 31. Although this specific embodiment shows an array of five sensors, a different number of sensors could be used, and the array may be one dimensional or two dimensional, that is, forming a matrix of sensors. The trade-off is accuracy versus cost. Fewer sensors means that average distance between the temporal artery and the closest sensor will be increased, therefore reducing the accuracy of the body temperature estimation. More sensors increase cost. The sensors 18 may be in one embodiment spaced approximately 10 mm apart. As shown in FIG. 7, to extend the physical region of temperature sensing, each sensor 18 may comprise a temperature sensor 40 is embedded within a disk 41 of material for example approximately 5 mm in diameter which possesses a high thermal conductivity. A flexible printed circuit board 12, 15 may be used to mount the sensors as well as to provide electrical connectivity between the sensors and a processor module 19. For clarity the flexible printed circuit board is shown in most figures as an upper 15 and lower 12 parts, but may be constructed as a single unit which is then folded over. The processor module 19 contains the electronic circuitry necessary to provide a means of measuring the outputs of the temperature sensors, processing that information as necessary, and transmitting it by wireless to a remote receiver 32. Although shown in the diagrams as a single entity, the processor module 19 represents the grouping of individual components necessary to implement the sensor interface, data processing, and the wireless link.

In the embodiment of FIGS. 3-6, a thin layer of flexible material 11 is attached to the bottom surface of the flexible printed circuit board 12, and contains holes 17 through which the sensor elements 18 protrude. The skin side of the material may be covered with an adhesive which allows the bandage to be temporarily affixed to the skin. Electrical leads 42 connect each temperature sensor 40 to the processor module 19 (see also FIG. 7). The combination of the slight protrusion of the sensor elements through the insulating layer, the use of the thermal conductive disk 41 to increase the surface area of the temperature sensor 40, and the adhesive properties of the bottom surface of the bandage help ensure that the skin temperature sensors make good thermal contact with the skin, and therefore can provide an accurate measurement of the underlying skin temperature. An outer thin layer of flexible material 16 is attached to the top surface of the flexible printed circuit board 15.

A second temperature sensor array 20, which may be of similar construction to the skin temperature sensor array 18, is arranged towards the outer (away from the skin) surface of the bandage. In one embodiment, the outer temperature sensor array is positioned such that the individual sensor elements of the second array 20 approximately overlay the corresponding sensor elements in the first array 18, but are separated from the first array elements by an intervening layer of material composed of two layers 13 and 14 for ease of construction. This intervening layer would typically be composed of insulating material so that a reasonable temperature difference can be measured between the first and second temperature array sensors under normal ambient conditions.

The second temperature sensor array 20 may be attached to the same flexible printed circuit board 15 and 12 as the first array 18. The flexible printed circuit board is folded over so that the sensor elements of the first and second array are aligned with each other. A composition of insulating material is sandwiched between the two sensor arrays 18 and 20. This composition may be formed of two layers for ease of construction. The bottom layer 13 contains a hole 23 to allow the folded flexible printed circuit board to pass through, and possibly a second cavity 25 to provide enough room for the processor module 19 to fit. The bottom layer ensures that the second array of sensor elements are separated from the first sensor array by a layer with well-controlled thermal properties. The upper layer 14 contains a hole 24 for the flexible printed circuit board and a hole 26 for the processor module, along with holes 21 for each of the temperature sensor elements of the second sensor array 20. The flexible printed circuit board also provides the electrical connectivity 22 between the sensor arrays 18 and 20 and the processor module 19 and any other components such as the battery and the antenna used for the wireless link. The components of the processor module are also mounted on the flexible printed circuit board.

The two temperature sensor arrays 18 and 20 plus the intervening material 13 and 14 allow the heat flow through the bandage to be estimated. It is this heat flow estimate that allows the core body temperature, as indicated by the temperature of the blood within the temporal artery, to be estimated from the skin temperature measurement.

Figure 8:
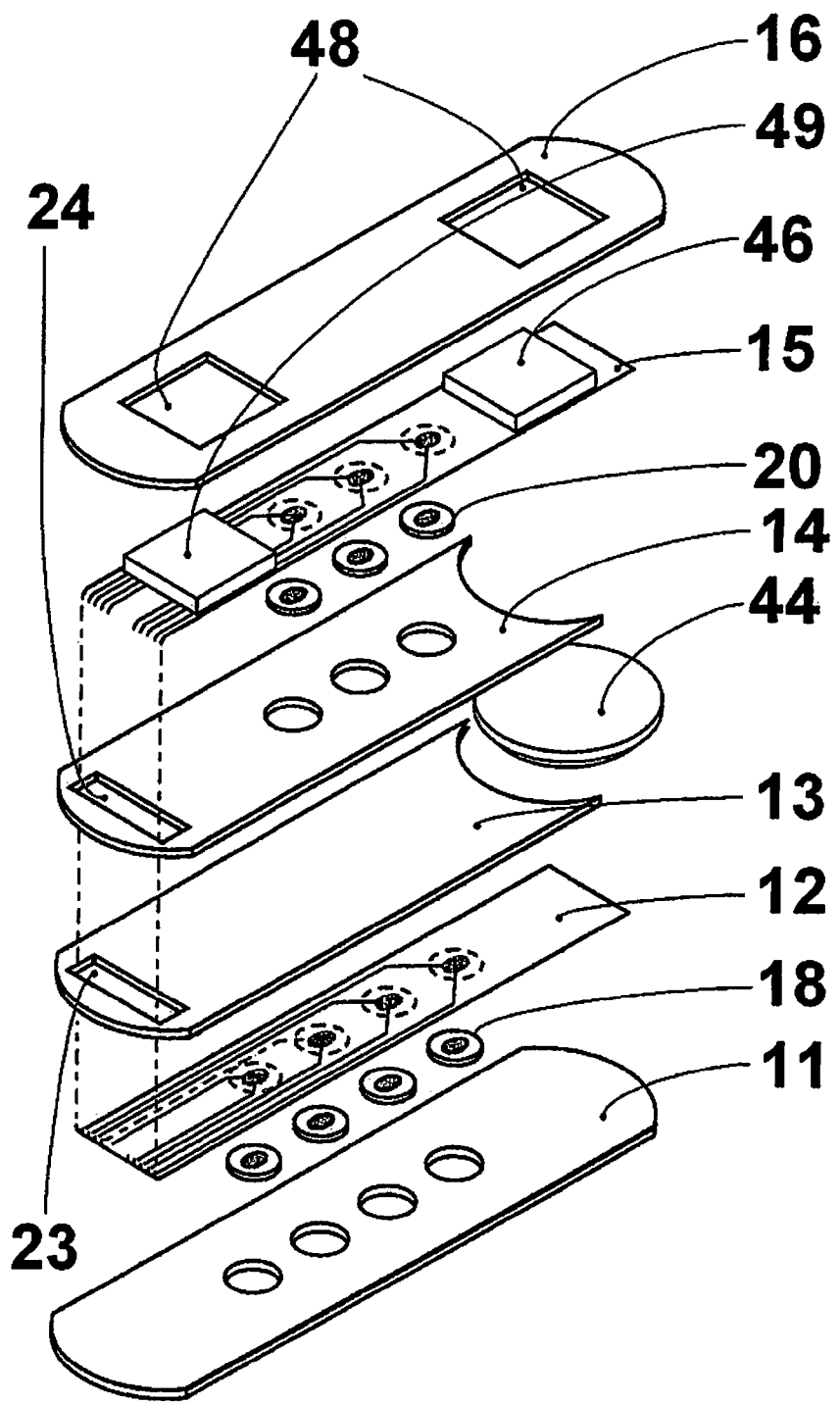
FIG. 8 shows an exploded view an embodiment of a bandage sensor.

An embodiment of the bandage thermometer 31 of FIG. 1 is shown in FIG. 8. A battery 44 lies between the upper and lower layers of the circuit board 15 and 12. The bottom layer 13 and upper layer 14 both are shaped to provide enough room for the battery 44. RF link electronics 46 and sensor interface electronics 49 attach to the circuit board 15 and each of the RF link electronics 46 and the sensor interface electronics 49 face away from the battery 44. Holes 48 are provided in the outer thin layer of flexible material 16 to provide room for the RF link electronics 46 and the processor module 19. The sensor interface electronics 49 and the RF link electronics 46 together function as the processor module 19 of FIG. 3.

In order to obtain a good estimate of the core body temperature, the skin temperature sensor with the highest temperature reading may be chosen to represent the skin temperature $T_{skin}$, since this should correspond to the location where the sensor is in closest proximity to the temporal artery. Once the appropriate skin temperature sensor has been selected, the outer temperature $T_{outer}$ can be measured from the temperature sensor in the second temperature array which is in closest physical proximity to the selected skin temperature sensor. The heat flowing out of the skin can now be estimated using $$q_{bandage} = h_{material}(T_{skin} - T_{outer}) \tag{2}$$

where $h_{material}$ is the thermal coefficient of conductivity of the material between the two temperature sensors, including that of the flexible printed circuit board 12 and that of the thermal insulating material layer 13 and 14.

Once the heat flow out of the skin is known, the heat balance equation can be solved to estimate the temperature of the underlying artery and hence the core body temperature. The heat balance law states that the heat flowing out of the body must equal the heat lost through the bandage, or $$q_{body} = h_{tissue}(T_{core} - T_{skin}) \tag{3}$$

Combining equations (2) and (3) leads to the heat balance equation $$h_{tissue}(T_{core} - T_{skin}) = h_{material}(T_{skin} - T_{outer}) \tag{4}$$

which reduces to the equation for core temperature (1) if $$\alpha = \frac{h_{material}}{h_{tissue}}. \quad (5)$$

The thermal conductivity coefficient $h_{material}$ can be measured experimentally and depends on the particular bandage construction and the material used. The tissue coefficient $h_{material}$ can be estimated from generally known thermal coefficients of tissue and an estimate of the average artery location. Alternately, the overall coefficient a can be determined experimentally using clinical trials, which is the preferred method.

Once the core body temperature is estimated, it is transmitted by wireless means to a remote receiver for monitoring.

In an alternate embodiment, the processor module 19 on the bandage may collect the raw sensor measurements and transmit that data to the remote receiver 32. At the remote receiver, the raw data is converted into a core body temperature estimate. By performing the majority of the data in the receiver, the power consumption of the processor on the bandage can be reduced and more sophisticated processing of the data can be implemented (error screening, averaging, etc.).

In yet another embodiment, the processing of the raw sensor data can be distributed between the bandage and the remote receiver. This allows the overall power of the bandage to be minimized by optimizing the power consumed by data processing versus power consumed by the wireless link. The more data processing is performed on the bandage the fewer bytes of data need to be transmitted. The optimum split between in the processing performed on the bandage versus the receiver will depend on the characteristics of the specific implementation of the processor module and the wireless transmission scheme used.

In order to minimize power consumption of the electronic circuitry located on the bandage, it may be desirable to transmit by wireless means all of the raw temperature sensor measurements to the remote receiver. The selection of the maximum skin temperature and corresponding outer temperature and subsequent calculation of the core temperature can then be performed by the processor at the receiver. Since the receiver can be line powered, power consumption is not a concern.

The remote receiver may have a means of entering a patient's core body temperature that was measured by some alternate means. The processor used to calculate the core body temperature can then use the alternately measured body temperature to adjust the coefficient, a, in order to calibrate a particular bandage to the specific patient. If the calculation of the core body temperature is performed on the bandage, a bidirectional wireless link can be used to upload the new value of a to the bandage, where it can be stored in some form of non-volatile memory.

An array may have any shape, and may be linear, two dimensional or three dimensional. The inner array establishes a baseline. The outer array may have the same or a different shape as compared with the first array. Preferably, the baseline is the skin temperature, and for this the sensors may be in thermal contact with the skin. The intervening material between the two arrays can be any suitable material or materials and may comprise several layers. A processor may include a transmitter and receiver. The bandage can be any shape.

The outside of the bandage experiences convective, radiative, and even evaporative heat loss (if wetted by sweat dripping on it), but this is unimportant, since the bandage sensor device in one embodiment uses a buried temperature sensor to directly measure the heat flux out of the skin surface. Therefore the bandage sensor device significantly reduces the variability of the coefficients in the heat balance equation. The core temperature can be estimated using $$T_c \simeq \frac{h_{bandage}}{h_{tissue}}(T_s - T_b) + T_s \quad (6)$$

where $h_{bandage}$ is the heat transfer coefficient which is dependent on thermal characteristics of the bandage (well controlled), and $T_b$ is the buried temperature within the bandage. Hence, equation (6) is equivalent to equation (1).

In an embodiment, for example, a small commercial very low power RF transceiver module operating at 2.4 GHz may be used to provide the wireless link, and a low-power microcontroller with an 8-channel ADC may provide the sensor interface. Temperature sensing is provided by an array of for example four 0.1° C. accurate thermistors arranged along the bottom surface of the bandage. Each thermistor may in some embodiments be mounted in a 5 mm diameter heat conductive disk, made for example of copper or aluminum, to increase the thermal capture area. To ease construction and to minimize the thermal shadowing caused by the skin sensor array, the array of three buried temperature sensors is offset from the skin sensors. The bandage is attached to the skin using adhesive tape. The entire bandage may be for example powered by a relatively small battery such as a CR2032 battery (3V, 220 mAh).

Immaterial modifications may be made to the embodiments of the bandage and method described here without departing from what is covered by the claims.

What is claimed is:

1. A device for the measurement of body temperature, comprising:
   a first array of temperature sensors arranged to determine a first temperature $T_{skin}$; and
   a second array of temperature sensors insulated from the first array, the second array of temperature sensors arranged to determine a second temperature $T_{outer}$; and a data processor configured to estimate core body temperature ($T_{core}$) using $T_{skin}$ and $T_{outer}$;
   wherein the first temperature is the highest temperature measured by the first temperature sensor array, and the second temperature corresponds to the sensor in closest physical proximity to the location where the highest temperature measured by the first temperature sensor array is, in operation, recorded.

2. The device of claim 1 in which the data processor configured to estimate the core body temperature ($T_{core}$) using the following formula $$T_{core} = T_{skin} + \alpha(T_{skin} - T_{outer})$$

where $\alpha$ is a pre-determined scaling factor.

3. The device of claim 1 in which the second array of temperature sensors is insulated from the first array of temperature sensors by a layer of insulating material.

4. A device for the measurement of body temperature, comprising:
   a first array of temperature sensors arranged to be placed in thermal contact with skin;
   a second array of temperature sensors insulated from the first array by a layer of material;

an electronic circuit for converting output from the first array and the second array into digital representations of sensor output;

an electronic circuit for wirelessly transmitting the digital representations of sensor output;

a wireless receiver to receive the digital representations of sensor output; and a data processor configured to define digital representation of sensor output of the temperature sensor from the first array that measures the highest temperature as $T_{skin}$, and configured to define as $T_{outer}$ digital representation of sensor output of the temperature sensor from the second array which is in closest physical proximity to the temperature sensor from the first array that measures the highest temperature; and the data processor being configured to estimate the core body temperature ($T_{core}$) using the following formula $$T_{core} = T_{skin} + \alpha(T_{skin} - T_{outer})$$

using the two selected temperatures ($T_{skin}$ and $T_{outer}$), and a scaling factor $\alpha$.

5. The device of claim 4 further comprising a means of displaying the estimated core temperature.

6. The device of claim 4 further comprising a means of retransmitting, by wired or wireless means, the estimated core temperature to other patient information processing/gathering system.

7. The device of claim 4 in which the first array, the second array and the processor are incorporated in a flexible carrier having an adhesive face for affixation to a body.

8. The device of claim 4 in which the temperature sensors of at least the first array are each in thermal contact with a disk of material of high thermal conductivity which increases the physical region for which the respective temperature sensors provide a measurement.

* * * * *